(12) United States Patent
Banks

(10) Patent No.: US 7,095,500 B2
(45) Date of Patent: Aug. 22, 2006

(54) INTERCHANGEABLE TIP-OPEN CELL FLUOROMETER

(75) Inventor: Rodney H. Banks, Aurora, IL (US)

(73) Assignee: Nalco Company, Naperville, IL (US)

( * ) Notice: Subject to any disclaimer, the term of this patent is extended or adjusted under 35 U.S.C. 154(b) by 304 days.

(21) Appl. No.: 10/769,631

(22) Filed: Jan. 30, 2004

(65) Prior Publication Data

US 2005/0168741 A1 Aug. 4, 2005

(51) Int. Cl.
*G01N 21/64* (2006.01)

(52) U.S. Cl. ............... 356/417; 250/461.1; 356/73

(58) Field of Classification Search ............... 356/317, 356/318, 417, 73; 250/458.1, 459.1, 461.1, 250/461.2

See application file for complete search history.

(56) References Cited

U.S. PATENT DOCUMENTS

| | | | | |
|---|---|---|---|---|
| 2,663,801 | A | * 12/1953 | Slavin et al. | 250/365 |
| 4,084,905 | A | * 4/1978 | Schreiber et al. | 356/317 |
| 4,301,372 | A | 11/1981 | Giering et al. | |
| 4,577,110 | A | * 3/1986 | MacBride et al. | 250/461.2 |
| 4,783,314 | A | 11/1988 | Hoots et al. | |
| 4,804,850 | A | * 2/1989 | Norrish et al. | 250/459.1 |
| 4,992,380 | A | 2/1991 | Moriarty et al. | |
| 5,994,707 | A | 11/1999 | Mendoza et al. | |
| 6,060,318 | A | 5/2000 | Moeggenborg et al. | |
| 6,255,118 | B1 | 7/2001 | Alfano et al. | |
| 6,280,635 | B1 | 8/2001 | Moriarty et al. | |
| 6,329,165 | B1 | 12/2001 | Chattoraj et al. | |
| 6,369,894 | B1 | 4/2002 | Rasimas et al. | |
| 6,490,030 | B1 | * 12/2002 | Gill et al. | 356/71 |
| 6,670,617 | B1 | 12/2003 | Banks | |
| 6,685,840 | B1 | 2/2004 | Hatch | |
| 2002/0054288 | A1 | 5/2002 | Kim et al. | |

FOREIGN PATENT DOCUMENTS

WO WO 03/060461 A2 7/2003

OTHER PUBLICATIONS

"SCUFA Submersible Fluorometer Performance Testing", www.turnerdesigns.com/t2/esci/s_0039., 11 pages, Dec. 1, 2003.
"SCUFA Submersible Fluorometer Performance Testing", www.turnerdesigns.com/t2/esci/s_0039., 9 pages, Jun. 14, 2004.
SCUFA User's Manual, Turner Designs, 47 pages, Apr. 15, 2002.
K.-H. Mittenzwey, G. Sinn, R. Hiersigk, M. Krause, P. Lenz, L. Pfeil, J. Rauchfuss, G. Streich, "A portable absorption-fluorometer for detection of organic substances in fluids", Fresenius' Journal of Analytical Chemistry, p. 355, 1996. (Abstract only).

(Continued)

*Primary Examiner*—F. L. Evans
(74) *Attorney, Agent, or Firm*—Thomas M. Breininger

(57) ABSTRACT

Described and claimed is an interchangeable tip-open cell fluorometer comprising a housing and a fluorometric probe tip interchangeably connected to the housing, the probe tip including a probe tip housing defining an open cell and enclosing a probe optical arrangement, the probe optical arrangement including an excitation source and a fluorescence detector wherein the excitation source is aimed directly into the fluorescence detector such that a sample can be fluorometrically detected. Also claimed is a method of using this interchangeable tip-open cell fluorometer for detecting fluorescent signals emitted by one or more fluorophores from samples from a natural or industrial water system. The fluorometer, when coupled with a controller, is capable of monitoring and optionally controlling an industrial process or system.

33 Claims, 5 Drawing Sheets

OTHER PUBLICATIONS

Robert F. Chen, "A laser-based fiber-optic fluorometer for in situ seawater measurements", Ocean Science and Technology, pp. 189-209, 2000. (Abstract only).

J. Bloch, B. Johnson, N. Newbury, J. Germaine, H. Hemond, J. Sinfield, "Field test of a novel microlaser-based probe for in situ fluorescence sensing of soil contamination", Society for Applied Spectroscopy, pp. 1299-1304, 1998. (Abstract only).

T Vo-Dinh., "Development of a DNA biochip: principle and applications", Sensors and Actuators B: Chemical Ysensors Actuators B: Chem., vol. B51, pp. 52-59. (Abstract only).

Maofan Qing, "The design of a novel field portable fluorescence spectrophotometer", Current Developments in Optical Design and Optical Engineering III, pp. 140-145, 2000. (Abstract only).

* cited by examiner

INTERCHANGEABLE TIP-OPEN CELL FLUOROMETER

FIELD OF THE INVENTION

The present invention relates generally to analytical devices and methods for monitoring and/or controlling natural or industrial processes or systems. More specifically, the present invention relates to an interchangeable tip-open cell fluorometer for detecting fluorescence emitted by a sample derived from a natural or an industrial process or system such that the process or system can be monitored and, optionally, controlled.

BACKGROUND OF THE INVENTION

A fluorometer is an analytical device that essentially comprises a light source, a means of selecting the desired excitation wavelength range, a sample cell, a means of selecting the desired emission wavelength range, and a detector. A spectrofluorometer is a specific type of fluorometer where the means for selecting the excitation and/or emission wavelength range is performed by a grating. A grating acts to disperse a continuum of light into its components. Spectrofluorometers may be further subdivided into scanning spectrofluorometers, those that use a mechanical means to scan the wavelength spectrum based on the position of the grating relative to the excitation source and/or emission (this describes a standard laboratory model fluorometer), or fixed spectrofluorometers where the grating is fixed with respect to the emission. The emission (fluorescence) is then directed to an array of detectors. The array of detectors could be charge coupled devices, usually abbreviated "CCD" or the array of detectors could be photodiodes. The detectors are then calibrated in the appropriate wavelength units. A commercial device such as this is available from Ocean Optics (available from Drysdale and Associates, Inc., P.O. Box 44055, Cincinnati, Ohio 45244 (513)831-9625). This type of fixed spectrofluorometer still requires the appropriate excitation wavelength selection device, which could be a grating or filter.

The fluorometers that are most suitable for use under field conditions are not grating spectrofluorometers, rather, they are filter-based fluorometers. A filter-based fluorometer uses a filter to exclude all but the selected wavelength range. In general, currently available and known filter-based fluorometers have one channel with this channel containing an optically appropriate cell.

A light source and an optional excitation filter, are positioned on one side of the optically appropriate cell, and an emission detector and an emission filter are positioned on another side of the optically appropriate cell. A reference detector may optionally be present. Because fluorescence is isotropic, in general, fluorometers are configured to detect any fluorescent light emitted from the fluorophore at a 90° angle from the light source in order to minimize collection of any spurious excitation light.

The excitation filter permits light of the chosen excitation wavelength range to pass through the filter and into the cell. When conducting off-line batch testing, a sample of, for example, water from a natural or an industrial water system is placed and held in the optically appropriate cell. When conducting on-line testing, the sample of water can flow through the optically appropriate cell. The light is absorbed by a fluorophore present in the water sample, which, in turn, emits a fluorescent light (hereinafter known as a fluorescent signal) having the same or a longer wavelength than the excitation light. The emission filter, which is positioned between the emission detector and the optically appropriate cell, is chosen so as to permit only the light emitted by the fluorophore (the fluorescent signal of the fluorophore) to pass through the filter to the emission detector.

The use of fluorophores in industrial water systems or in hydrology in general is known. The use of inert fluorescent tracers for determining the hydraulic losses in an industrial water system is known. Furthermore, using fluorescent tracers for controlling additive or product dosage to a recirculating or once-through cooling water system is also known (see U.S. Pat. No. 4,783,314). In this method, a fluorescent tracer is combined with one or more additives in a known proportion of tracer to additive(s) and then the mixture is added to the water of a cooling system. A fluorometer is then used to detect the presence and concentration of the fluorescent tracer in the cooling water and therefore the presence and concentration of the amount of additive.

There will always be a continuing need for new and improved fluorometers to be available for use in the challenging area of monitoring and controlling industrial water processes.

SUMMARY OF THE INVENTION

The first aspect of the instant claimed invention is an interchangeable tip-open cell fluorometer comprising:
  a housing and a fluorometric probe tip interchangeably connected to the housing, the probe tip including a probe tip housing defining an open cell and enclosing a probe optical arrangement, the probe optical arrangement including an excitation source and a fluorescence detector wherein the excitation source is aimed at the fluorescence detector such that a sample can be fluorometrically detected.

The second aspect of the instant claimed invention is a method of fluorometrically detecting fluorophores present in a sample, the method comprising the steps of:
  a) providing a fluorometer, the fluorometer comprising a housing and a fluorometric probe tip interchangeably connected to the housing, the probe tip including a probe tip housing defining an open cell and enclosing a probe optical arrangement, the probe optical arrangement including an excitation source and a fluorescence detector wherein the excitation source is aimed at the fluorescence detector such that a sample can be fluorometrically detected;
  b) providing one or more samples derived from a natural or industrial process stream;
  c) using the fluorometer to detect the fluorescent signals of the fluorophores in the samples; and
  d) operating a controller in such a way that the fluorescent signals detected by the fluorometer are used by the controller to monitor and/or control the natural or industrial process from which the samples are taken.

DETAILED DESCRIPTION OF THE PRESENTLY PREFERRED EMBODIMENTS

Figure 1:
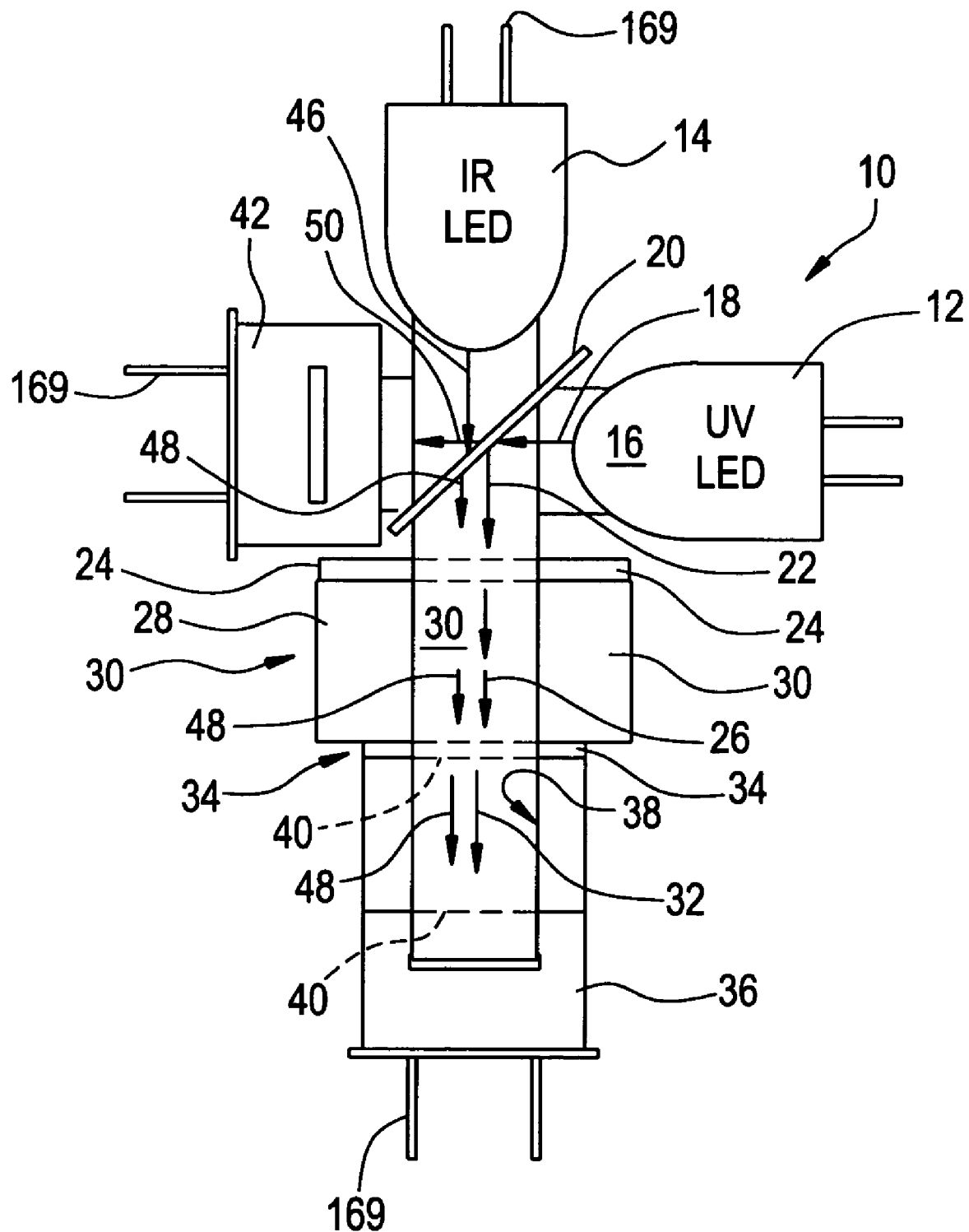
FIG. 1 is a cut away sectional view of an interchangeable probe tip for a fluorometer made in accordance with the present invention.

Throughout this patent application the following words have the indicated meanings:

A "fluorophore" is: a molecule that, upon absorption of a photon of energy (hv) that results in an electron being promoted from the molecular electronic ground state ($S_0$) to an electronic excited state ($S_1$ or $S_2$ or $S_3$) and subsequently relaxing to the lowest vibronic state of excited state $S_1$, emits a photon of energy "E" (hv) that is lower in energy (though longer in wavelength) than was absorbed. Note that this relationship can be illustrated with the equation: $E_{(absorption)} > E_{(fluorescence)}$. This emission of energy results in the molecular electronic state being returned to the ground state ($S_0$). The overall process results in emission of fluorescent photons in an isotropic distribution. The fluorophores capable of being detected by the instant claimed fluorometer must be capable of absorbing excitation light in the wavelengths of from about 200 nm to about 1200 nm and emitting it at a longer wavelength than the excitation light.

"Inert" refers to the fact that an inert fluorophore is not appreciably or significantly affected by any other chemistry in the cooling water system, or by the other system parameters such as metallurgical composition, microbiological activity, biocide concentration, heat changes or overall heat content. To quantify what is meant by "not appreciably or significantly affected", this statement means that an inert fluorophore has no more than a 10% change in its fluorescent signal, under conditions normally encountered in cooling water systems. Conditions normally encountered in cooling water systems are known to people of ordinary skill in the art of cooling water systems.

"Isotropic" refers to the fact that if a moiety is considered a point source, and excitation light is directed at the moiety, fluorescent light is emitted equally in all directions, creating, in effect, a sphere in 3 dimensions.

"nm" means nanometers; which are $10^{-9}$ meters.

The present invention provides an interchangeable tip-open cell fluorometer. This interchangeable tip-open cell fluorometer includes one or more probe tips that can be interchangeably used with respect to the same fluorometer. At least one of the probe tips includes an optical arrangement that allows for the fluorometric detection of a sample in a measuring cell associated with the fluorometer such as a measuring cell in an open or flow cell configuration. In general, the probe tip optical arrangement includes an excitation source and a fluorescence detector such that excitation source is aimed at the fluorescence detector, such as directly at the detector in a 180° arrangement or substantially approximate 180° arrangement. This effectively provides a sleek and simple design that can be effectively used to detect, monitor and/or control industrial or natural streams based on a fluorometric measurement from a sample derived from same. It should be appreciated that the present invention contemplates an arrangement with respect to the excitation source and the fluorescence detector that can deviate from a 180° arrangement as described below in greater detail.

The interchangeable tip-open cell fluorometer of the present invention can provide a low-cost alternative to conventional fluorometers. In an embodiment, the fluorometer of the present invention is provided in a flashlight-style that can be hand-held and shaped in any suitable way, such as a cylindrical tube shape. In this regard, a measurement can be taken by dipping the interchangeable tip of the fluorometer of the present invention into a process water sample, for example, cooling water treated with treatment chemicals and using fluorometers for detecting fluorophores, pushing a button, and reading the product level, such as in parts per million (ppm) on a display.

With this fluorometer, the design emphasis is on minimal cost for small accounts and ease of use for unskilled operators. The cylindrical tube-shape has many desirable functional features including battery operation, numerical readout, two-point calibration, compensation for sample temperature, turbidity, and fouling of the optical surfaces, communications to Palm computer or the like for downloading of stored data, a unique, self-identifying fluorometer probe tip and the like. The fluorometer of the present invention can be made with a process control output and connector, for controlling a chemical feed pump, data logging and/or for performing other suitable process monitoring and/or control activities. For example, the fluorometer of the present invention can be adapted to alert the user when cleaning of the tip is required.

An important aspect of the present invention is the interchangeable probe tip. In general, the probe tip provides a small, self-contained fluorometer with built-in optics and circuitry, such as for type identification, detectors, light sources, temperature measurement and the like. The probe tip is constructed such that it is readily pluggable into the fluorometer housing. This makes it easily replaceable with another probe tip whenever a different probe tip with different optics is necessary to account for changes in the sampling environment, such as for measuring the fluorescence derived from different fluorophores, tip damage and/or the like. Upon replacing one interchangeable tip for another interchangeable tip, the fluorometer is ready-for-use with minimal, or effectively no, added effort required from the operator. This is a huge practical advantage of the instant claimed invention, especially when compared to the effort required to set up and use two different fluorometers.

In this regard, the probe tip contains virtually all of the electronics and optics to perform the fluorescence measurements. For example, proper gain can be built into the electronic configuration associated with the probe tip, thus relieving the main unit from having to adjust gain settings. Further, noise interferences can be minimized by having the electronics inside of the probe tip. The excitation source, such as a light emitting diode (LED) source, can be configured to have its own series resistor so that the main unit does not have to regulate LED current.

The probe tip also optionally can include a thermistor. It is preferred that the probe tip include a thermistor to measure sample temperature for correction of fluorescence intensity. By choosing different thermistor resistances based on, for example a temperature of 25° C., the probe tips are effectively self-identifying without added cost or complexity. In other words, each probe tip can include a thermistor with a resistance that is specific to the respective probe tip. Once the probe tip is plugged into the fluorometer housing and the thermistor resistance is made known, the specific optical and electronic arrangement with respect to the probe tip can be identified, thus allowing the interchangeable tip-open cell fluorometer to be ready-for-use.

As previously discussed, the probe tip has an optical arrangement that provides a linear and slim profile for the fluorometer. In this regard, the excitation source of the probe tip is aimed at the fluorescence detector. For example, the excitation source and/or the light that emits therefrom and the fluorescence detector can be configured in a 180° arrangement or acceptable deviations thereof. This is different from conventional one-channel-sample fluorometers where detection of the fluorescent light emitted from the fluorophore is at a 90° angle from the light source as previously discussed. Based on these differences, the interchangeable tip-open cell fluorometer of the present invention can provide a number of advantages over conventional one-channel-sample fluorometers including, for example, a sleek and simple design, selectable sensitivity, accurate compensation for turbidity and window fouling, and the like as described below.

The fluorometer of the present invention makes use of a specific type of optical filters, such as a thin-film optical filter with the requisite optical, mechanical and chemical properties necessary to enhance the fluorescent detection capabilities. The physical attributes of the filters can also enhance the detection sensitivity as compared to quartz, glass sample cells, cuvettes or the like that can contribute to unwanted light scattering such that the sensitivity and concentration range can be reduced. In this regard, the measured sample is in direct contact with the filters that define the measuring volume. Thus the use of the term "open cell" as a descriptor of the fact that it is the filters themselves that form the outer boundaries of the sample cell and there is no other structure involved in the sample cell, except for the outer walls of the housing itself.

The filters are required to be made from a material or combination of materials that are chemically inert and provide a hard surface such that chemical and brush cleaning of the cell can be performed when it becomes necessary. By designing the optical filters for a water interface on the sample side and air interface on the internal side, performance of the filters can be optimized for analyzing low levels of fluorophores.

The fluorometer of the present invention can include a variety of different components fashioned in any suitable configuration depending on the application. It can be configured as a stand alone unit or it can be interfaced with one or more additional process components for monitoring and/or control purposes in any known and suitable way. The interchangeable tip-open cell fluorometer can be adapted for detection purposes in any suitable way, such as for grab sampling purposes, in-line detection, in-process detection and/or the like.

In general, the fluorometer includes a fluorometric probe tip that is interchangeably connected to a housing. The fluorometric probe tip includes an excitation light source. The excitation source can include any suitable type of light source, such as a monochromatic light source, polychromatic light source and the like. For example, the excitation source can include a LED source, a laser source and the like. The LED source can emit light of varying wavelengths, such as an IR LED, a UV LED, a blue LED and/or the like.

The excitation source generates a collimated beam of excitation light. The excitation light passes through a filter in the probe tip and into a measuring cell with an open-cell configuration defined by the probe tip housing and the surface of the excitation light filter and the surface of the emission light filter. The sample is in direct contact with the filters as previously discussed. This allows the excitation light to project into the sample within the measuring cell whereupon fluorescence is produced due to the presence of one or more fluorophores in the sample. The emitted fluorescence then passes through an additional filter and is directed to a fluorescence detector for detection purposes. The additional filter also acts to effectively block the excitation light from passing to the fluorescence detector. This allows the fluorescence of the sample to be measured with precision, sensitivity and accuracy despite the fact that the excitation light is directed at the fluorescence detector, such as directly at the fluorescence detector in a 180° optical arrangement. As previously discussed, this optical arrangement provides a number of advantages as compared to fluorometers that use a conventional 90° optical arrangement.

The sample can emit fluorescent light due to the presence of one or more fluorophores within the sample as discussed above. Regarding the description of the fluorophores capable of being detected by the instant claimed fluorometer, it is necessary to note that in order to be detectable by the instant claimed fluorometer, the fluorophore must be capable of absorbing light in the wavelengths of from about 200 nm to about 1200 nm and emitting it at a slightly longer wavelength. Preferably, the fluorophores absorb light in the wavelengths of from about 350 nm to about 800 nm. The fluorescence detector measures an amount of fluorescence that can be correlated to a concentration of the fluorophore in the sample. In an embodiment, the fluorescence detector can measure an intensity of the fluorescence that can be equated to a concentration of the fluorophore as generally understood to one of skill in the art.

The filters can be made of any suitable material. In general, the optical, mechanical and chemical properties of the filter are provided and required as follows according to an embodiment. With respect to optical properties, the filters are required to have a high transmittance in pass band areas for the excitation light (i.e., UV LED) or the emitted fluorescence. As mentioned above, the first filter essentially allows all of the excitation light to pass therethrough and into the sample. Then, the emitted fluorescence from the sample can pass through the second filter all the while the excitation light is effectively blocked from passing through the second filter and inevitably to the detector. Thus, this ensures that the interference effects of the excitation light with respect to the fluorescent measurement are effectively eliminated, or at least greatly reduced. This effect can be further enhanced if the pass bands of the filters are sharp and deep cut.

If a second light source is used, the optical properties of the filters allow the second light in a sufficient amount to pass through both filters and at a different wavelength than the light emitted from the excitation source. In this way, the second light source can be used to correct for fouling, turbidity and/or other like effects that can adversely impact the detection capabilities of the fluorometer as described in greater detail below.

With respect to mechanical properties, the filter includes an exposed surface that is hard such that it can withstand general use, such as cleaning, brushing, abrasive particles in the sample and the like. This is an important quality due to the fact that the filters act to define the open cell configuration of the measuring cell according to an embodiment of the present invention. In this regard, the sample is in direct contact with the filters and thus must be able operate effectively under normal process conditions. The filters are also effectively chemically inert. In this way, the filters should not be reactive, such as with respect to the sample, cleaning solutions and the like. Having the filters define the measuring cell, light scattering due to glass sample cells in conventional fluorometers is effectively eliminated.

The filters can also be used to adjust the sensitivity of the fluorescent detection. In this regard, the distance between the filters can be varied and thus effectively acts to adjust sensitivity. This may be useful if the measured samples may require different levels of detection sensitivity. For example, a more concentrated sample of fluorophores may require a lower sensitivity to enhance detection capabilities. In this regard, the spacing between the filters can be decreased to create less volume of measured sample, thus lowering the sensitivity with respect to the detection of same. For less concentrated samples, the spacing may be increased to increase sensitivity. Thus, the present invention can be readily adapted to adjust for varying levels of sensitivity depending on the application. This sensitivity adjustment cannot be achieved with the conventional 90° optical arrangement.

Preferably, the filter includes a layered structure. In general, the filter provides a low pass filter layer and a high pass filter layer that are separated by a substrate layer, such as a glass substrate. This structure allows for the fluorescence emission to pass to the detector via the filter while the excitation light is effectively blocked from doing so. The filters are commercially available as Brightline™ at Semrock, Incorporated, 3625 Buffalo Road, Suite 6, Rochester, N.Y. 14624 (585)594-7017. It should be appreciated that a commercially available filter material may be required to be modified and customized with respect to the optical, mechanical and chemical properties of the filter depending on the application.

The interchangeable probe tip can include additional other and suitable components that can further enhance its detection capabilities. For example, the probe tip can include a reference detector. This is used to measure a portion of the excitation light source during fluorescent detection. In this regard, the reference detector can be used to compensate for variations in the excitation light emission due to, for example, changes in current associated with the excitation light source, temperature changes, aging, device to device variability, production tolerances and/or the like. This can be done in a number of suitable ways. For example, the fluorescence measurement associated with the fluorescence detector can be divided by the reference detector measurement to provide a normalized fluorescent measurement. This, in essence, subtracts outs the variation effects with respect to the excitation light source as discussed above. In an embodiment, the reference detector and the fluorescence detector include the same type of detector. This effectively alleviates any variability in detection between the reference detector and the fluorescence detector that may be due differences in the type of detector that is used. It should be appreciated that the reference detector can also be applied to effectively eliminate any variability in the second light source in any suitable way, such as in a similar way as discussed above with respect to the excitation light source.

Further, the interchangeable probe tip can include an aperture. The aperture can be made of any suitable material and sized and configured in any suitable way including a cylindrical tube shape. In an embodiment, the fluorescence emission passes to the detector via the aperture. In this way, the aperture can be effectively sized and shaped to minimize the effects of turbidity on the fluorescent detection capabilities of the fluorometer. Turbidity can cause light scattering that can be detected and thus interfere with the fluorescent measurement. As the aperture size is decreased, this should minimize light scattering effects due to turbidity. However, the aperture size should not be too small such that the emitted fluorescence or sufficient portion thereof is prevented from passing to the fluorescence detector.

In an embodiment, the interchangeable probe tip includes two light sources, an excitation light source and a second light source that does not induce fluorescence. The second light source can be used to correct for effects on the fluorescent measurement due to fouling, turbidity and/or the like. The excitation source is dedicated for direct fluorescence measurement. This source emits a collimated beam of light into the sample whereupon fluorescence is emitted based on the amount of fluorophore in the sample. The fluorescence emission then passes to the fluorescence detector via the filter where the excitation light is effectively blocked from passing to the fluorescence detector as previously discussed.

Once fluorescent detection has been made, the excitation source is turned off and the second light source is turned on. The light emitted from the second light source is a different wavelength than the light emitted from the excitation source so as not to induce fluorescence. In an embodiment, the excitation source includes a UV LED, and the second light source includes an IR LED. The second light source emits light into the fluorescence detector via the filters and sample. The second light emission is preferably directed along a path that corresponds to the same path along which the light from the excitation source was passed. In an embodiment, the first and second light emissions pass along the same or substantially the same path. This allows the second light, once detected, to provide an accurate indication that corresponds to the amount of fouling, turbidity and/or other effects on the fluorescent measurement. In this way, the fluorescent measurement can be corrected in any suitable manner to account for such effects, thus enhancing the fluorescent detection capabilities. These corrections cannot be done with the conventional 90° optical arrangement.

Alternatively, the first and second light emissions can deviate from an emission path that is the same or substantially the same. Thus, the first and second light emissions can be configured to pass in sufficient portion along the same path such that correction with respect to fouling, turbidity and/or the like can be effectively, though less accurately, made. It should be appreciated that the first and second light sources can be configured in a number of suitable and different ways, some of which are described in greater detail below.

As previously discussed, the interchangeable tip-open cell fluorometer of the present invention can be configured in a number of suitable ways. As detailed below, a number of examples of the interchangeable probe tip are provided illustrative of the present invention.

EXAMPLES

Example One

Interchangeable Probe Tip with Normal, Parallel Beam Configuration

Turning to FIG. 1, an embodiment of the present invention is illustrated. The interchangeable probe tip 10 includes an excitation light source 12 and a second light source 14. The excitation source 12 includes an ultraviolet light emitting diode 16 (UV LED). The excitation source 12 emits a collimated excitation light beam 18 that is directed at a reflective member 20, such as a dichroic mirror or the like, as shown in FIG. 1. The reflective member 20 is reflective with respect to a substantial amount of the excitation light beam 18, such as about 98% reflective or less. The reflective member 20 is also transmissive with respect to the remaining portion of excitation light beam, such as about 2% transmissive or greater. The reflected portion 22 of excitation light associated with the excitation light source 12 is directed to a first filter 24 at an angle that is perpendicular or substantially perpendicular with respect to the first filter 24. The excitation light beam 26 passes into a measuring cell 28 where the sample 30 is provided in an open cell arrangement. The projection of the excitation light 26 causes a fluorescence emission 32 based on an amount of fluorophore in the sample 30. The fluorescence emission 32 passes through a second filter 34 and into a fluorescence detector 36 via an aperture 38 that has an opening 40 sized to receive the collimated beam of fluorescence emission 32 in at least a substantial amount. The fluorescence detector 36 then acts to measure the amount of fluorescence which can be correlated in any suitable manner to a concentration of the target fluorophore or fluorophores in the sample for monitoring and/or control purposes.

To enhance the detection capabilities of the fluorescent detection, the interchangeable probe tip includes a reference detector 42 that receives a portion of the excitation light 18 via the reflective member 20 as previously discussed. The reference detector 42 can be used to compensate for variations in the excitation light emission as discussed above.

The interchangeable probe tip 10 further includes a second light source 14 that is used for corrective purposes with respect to fouling, turbidity and/or the like as discussed above. The second light source 14 includes an IR LED source. This generates a collimated beam of light 46 that is directed to the reflective member 20. A substantial amount of the beam 46 is transmitted through the reflective member 20, as light beam 48, along the same or substantially the same path as the reflected excitation light beam 22. In an embodiment, about 98% or more of the light beam is transmitted through the reflective member 20 and into the measuring cell 28. The remaining portion of light beam 50 associated with the second light source 14 is reflected via the reflective member 20 into the reference detector 42 to compensate for variations in the second light source emission similar to the excitation source emission as previously discussed.

The transmitted amount of light beam 48 from the second light source 14 passes through the sample 30 and further passes through the second filter 34 in at least a substantial amount along the same or substantially the same path that the fluorescent emission 32 passes through the second filter 34. The amount of transmitted light associated with the second light source is then detected by the fluorescence detector 36. This measurement can be used in any known way to correct for changes in the fluorescent measurement due to fouling, turbidity and/or the like as previously discussed.

Example Two

Interchangeable Probe Tip with Straight-Through Beam Configuration

Figure 2:
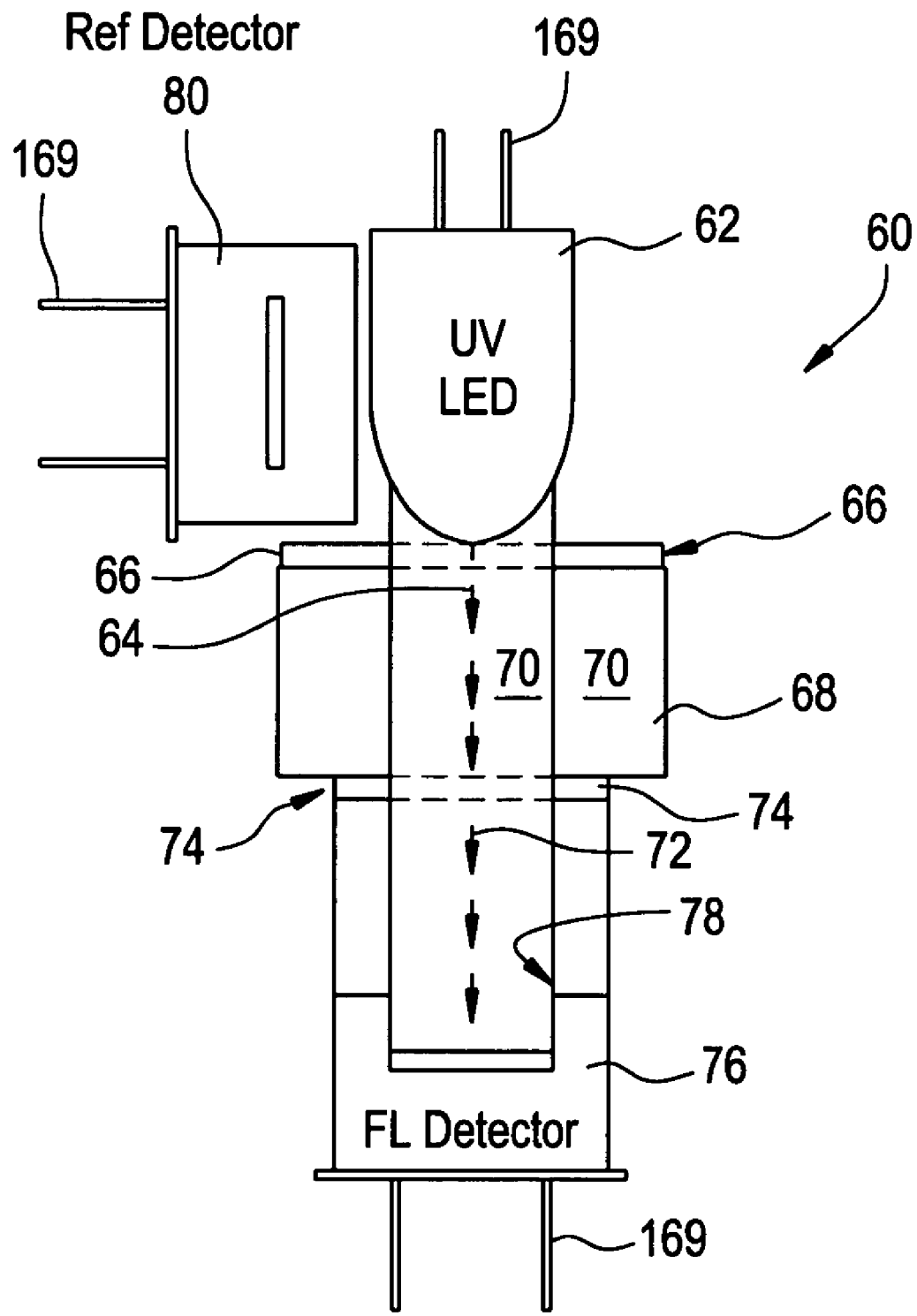
FIG. 2 is a cut away sectional view of another interchangeable probe tip for a fluorometer made in accordance with the present invention.

Turning to FIG. 2, another embodiment of the interchangeable probe tip according to the present invention is provided. The interchangeable probe tip 60 includes a single light source 62 that includes a UV LED source. The excitation source 62 emits a collimated light beam 64 through a first filter 66 and into a measuring cell 68 where the sample 70 is located. This causes fluorescence associated with an amount of fluorophore in the sample. The fluorescence emission 72 passes through a second filter 74 and into a fluorescence detector 76 for detection purposes. The fluorescence emission 72 passes through an aperture 78 to minimize the effects of turbidity on the detectable fluorescence. The aperture 78 is sized such that all or a substantial portion of the fluorescence emission passes therethrough and into the detector. The interchangeable probe tip further includes a reference detector 80 that can be used to measure a portion of the light derived from the excitation source. As previously discussed, this can be then used to account for variations in the excitation light source.

Example Three

Interchangeable Probe Tip with Double Angle Beam Configuration

Figure 3:
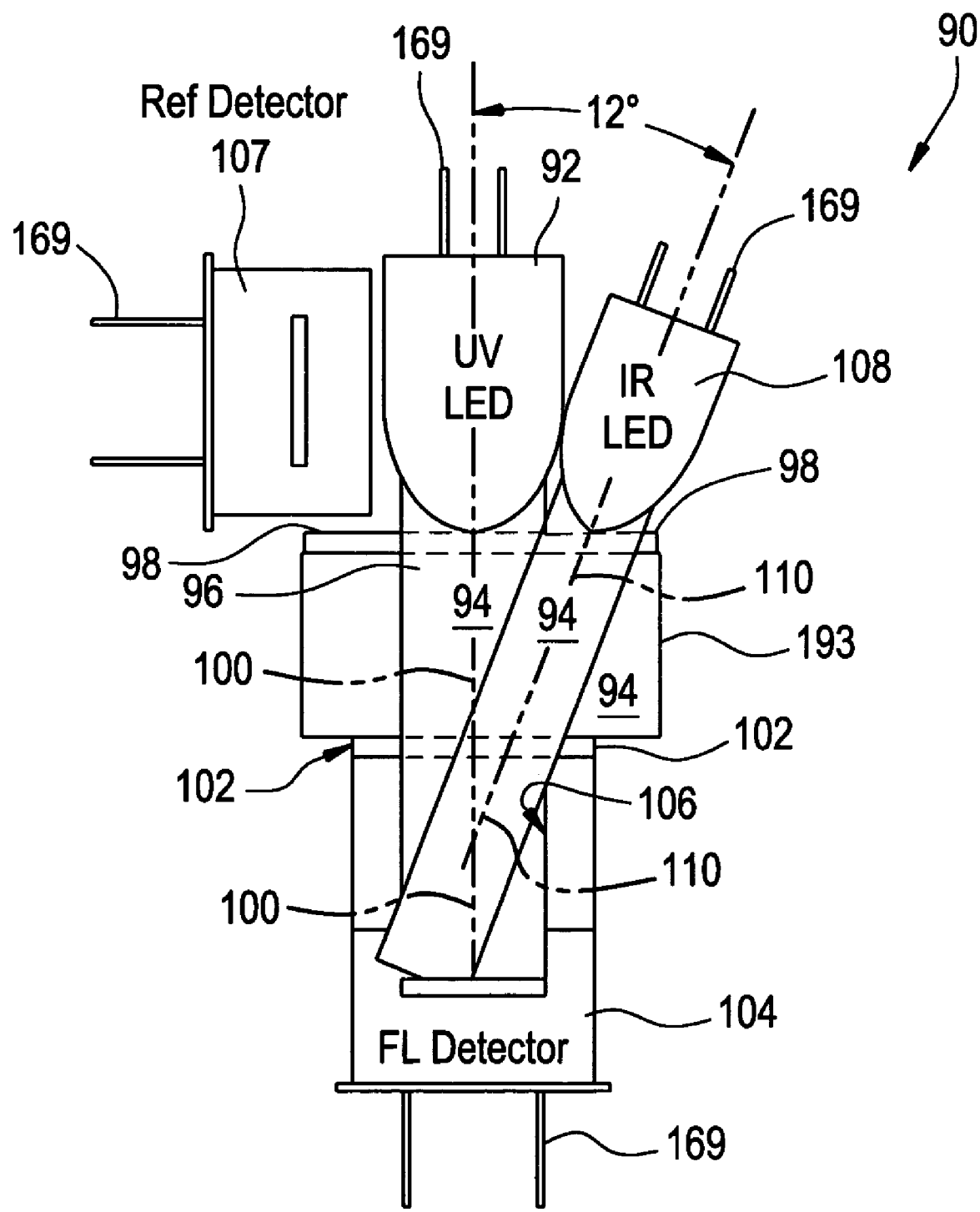
FIG. 3 is a cut away sectional view of yet another interchangeable probe tip for a fluorometer made in accordance with the present invention.

Turning to FIG. 3, another embodiment of the interchangeable probe tip is provided. The interchangeable probe tip 90 includes an excitation source 92 that includes a UV LED source. This is used to measure fluorescence in a sample 94 within a measuring cell 193 in a similar fashion as provided in EXAMPLE TWO. In this regard, the excitation light source 92 emits a collimated beam of light 96 into the sample 94 via a first filter 98 such that a fluorescence emission 100 is generated and then passes through a second filter 102 into a detector 104 via an aperture 106. The excitation light 96 is effectively blocked out or at least a substantial portion thereof from passing into the detector 104 due to the optical features of the filters as discussed above. Thus, the fluorescent measurement can be taken with minimal, if any, effect due to the excitation light. The probe tip further includes a reference detector 107 that detects a portion of the excitation light derived from the excitation source. This can also enhance the detection capabilities of the probe tip as previously discussed.

Further, the probe tip 90 includes a second light source 108. The second light source 108 includes an IR LED that generates a collimated beam of light 110. The light 110 passes through the first filter 98 at an angle offset from perpendicular to the first filter. For example, the angle is offset at about 12° or less from perpendicular or normal. In this way, the second source of light 110 passes through the sample, through the second filter 102 and into the detector 104 via the aperture 106 along a path that corresponds in a sufficient amount to the path through which the excitation light and fluorescent emission has passed. The detector then can measure the intensity of the second light source which can be used for corrective purposes as previously discussed. This demonstrates that the second source of light does not necessarily have to pass along the same path as the source of excitation light and/or emission therefrom in order to effectively act for corrective purposes due to fouling, turbidity and/or the like. Reference detector 107 can be used to measure a portion of the light from light source 108 to account for variations in light source 108.

Example Four

Interchangeable Probe Tip with Compound Angle Beam Configuration

Figure 4:
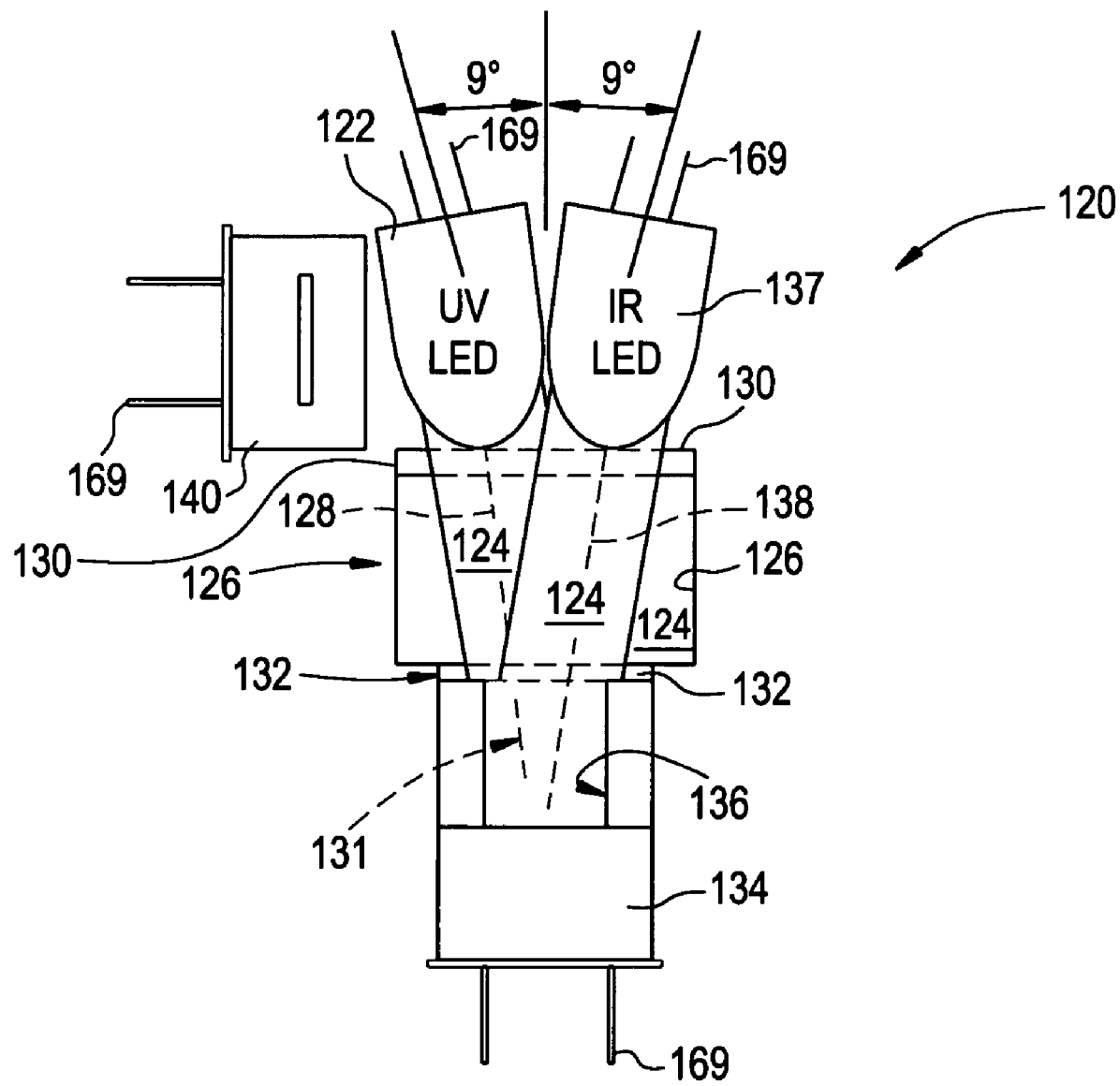
FIG. 4 is a cut away sectional view of still yet another interchangeable probe tip for a fluorometer made in accordance with the present invention.

Turning to FIG. 4, another embodiment illustrative of the interchangeable tip is provided. In general, this example provides another variation regarding the positioning with respect to a pair of light sources that can be used to enhance the fluorescent detection capabilities of the interchangeable probe tip.

The interchangeable probe tip 120 includes an excitation source 122 that includes a UV LED source. This is used to measure fluorescence in a sample 124 within a measuring cell 126. In this regard, the excitation light source 122 emits a collimated beam of light 128 into the sample 124 via a first filter 130 such that a fluorescence emission 131 is generated and then passes through the second filter 132 into a detector 134 via an aperture 136. The excitation light 128 passes through the first filter 130 at an angle offset from perpendicular, such as about 9° or less. The excitation light 128 is effectively blocked out or at least a substantial portion thereof from passing into the detector 134 due to the optical features of the filters as discussed above. Thus, the fluorescent measurement can be taken with minimal, if any, effect due to the excitation light.

Further, the probe tip 120 includes a second light source 137. The second light source 137 includes an IR LED that generates a collimated beam of light 138. The light 138 passes through the first filter 130 at an angle offset from perpendicular, such as about 9° or less with respect to the first filter 130. In this way, the second source of light 138 passes through the sample 124, through the second filter 132 and into the detector 134 via the aperture 136 along a path that corresponds in a sufficient amount to the path through which the fluorescent emission passed. The detector 134 then can measure the intensity of the second light source which can be used for corrective purposes as previously discussed. This further demonstrates that the second source of light does not necessarily have to pass along the same path as the source of excitation light and/or emission therefrom in order to effectively act for corrective purposes due to fouling, turbidity and/or the like.

The probe tip 120 further includes a reference detector 140 that detects a portion of the excitation light derived from the excitation source. This can also enhance the detection capabilities of the probe tip as previously discussed. Reference detector 140 can be used to measure a portion of the light from light source 137 to account for variations in light source 137.

Example Five

Self-Identifying Interchangeable Tip-Open Cell Fluorometer

Figure 5:
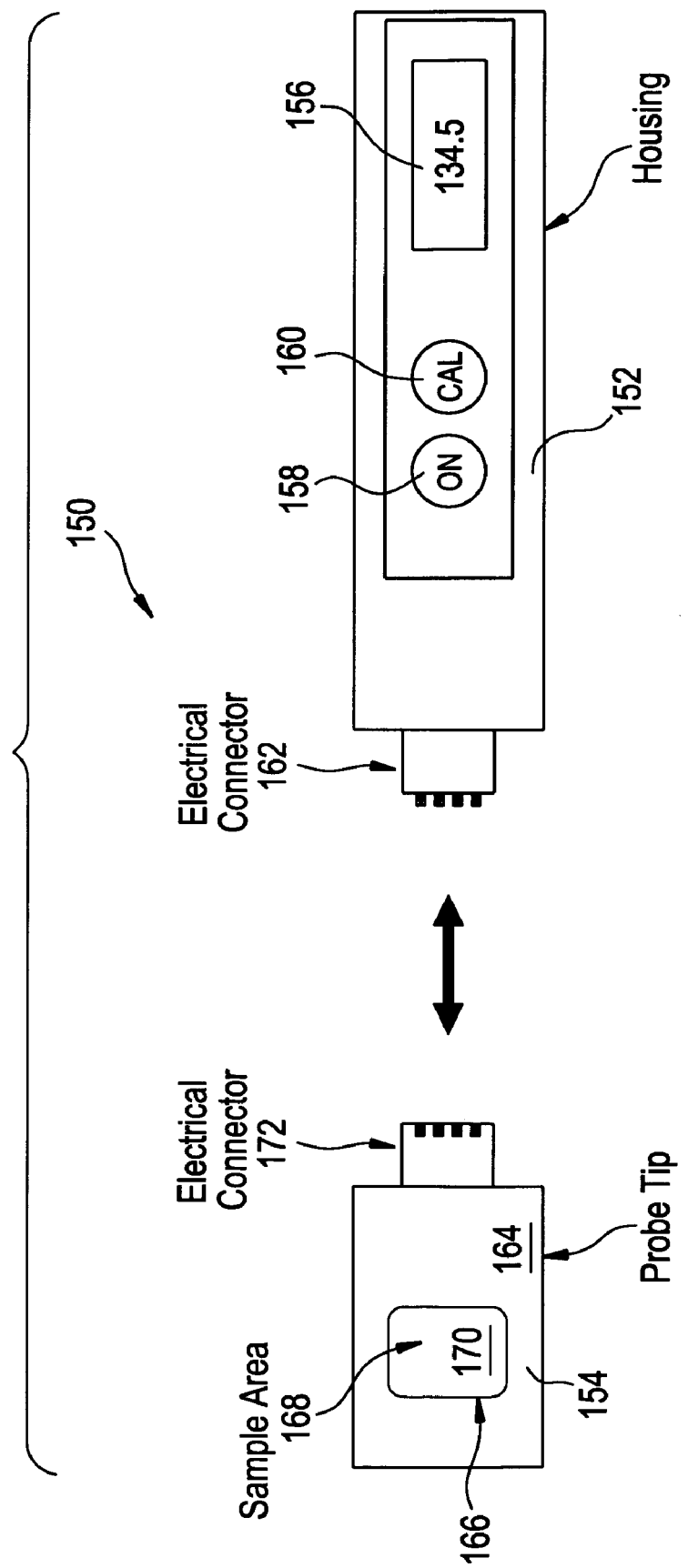
FIG. 5 is a sectional view of an interchangeable probe tip fluorometer made in accordance with the present invention.

As previously discussed, the fluorometer of the present invention has a self-identifying feature that allows the fluorometer to be ready-for-use once one probe tip is interchanged with another probe tip. Turning to FIG. 5, the fluorometer 150 includes a housing 152 and a probe tip 154. The housing electronics (not shown) can be configured in any suitable way to power the fluorometer 150. In this regard, the fluorometer can be battery operated. In the alternative, the fluorometer can be operated by an external power source that is electrically connected to the fluorometer, such as through the housing. The housing 152 can include a display 156 for monitoring the fluorescent measurements. At least a number of the functions of the fluorometer can be automated, such as through a switch. For example, the housing 152 can include an on/off switch 158 and a calibration switch 160 for operation in calibration mode as shown in FIG. 5. The wiring from the electronics of the housing 152 leads to an electrical connector 162 of any suitable type.

The interchangeable probe tip 154 has a housing 164 with an opening 166 that defines a measuring cell 168 within which a sample 170 can be fluorometrically measured as previously discussed. The probe housing encloses the optics and electronics of the probe tip which can be configured in any suitable way such as illustrated above. The wiring of the electronics, such as the leads 169 to the detectors, light sources and the like connect to the electrical connector 172 of the probe tip 154. This allows the probe tip 154 to be pluggable into the housing 152 via mating of the electrical connector 172 of the probe tip 154 and the electrical connector 162 of the housing 152.

Once the probe tip is plugged into the housing, the fluorometer is effectively ready for use. The probe tip includes a thermistor (not shown). The optical and electronic arrangement of the probe tip is associated with a respective thermistor that has a specific resistance as previously discussed. This allows the fluorometer to recognize what type of probe tip is being used once a probe tip has been interchanged with another probe tip, thus enabling it ready for use.

It should be appreciated that the self-identifying property of the interchangeable tip-open cell fluorometer can be configured in any suitable way. For example, the self-identifying features of the present invention can include the same or similar features with respect to the "smart" probe as disclosed in U.S. Pat. No. 6,556,027 that issued on Apr. 29, 2003, which is herein incorporated by reference in its entirety.

The interchangeable probe tip can include any suitable type of optical and electrical arrangement for purposes of fluorescent detection, examples of which have been discussed above. In addition to fluorescence, the fluorometer can be adapted to take additional other measurements, such as with respect to turbidity, colorimetry and the like. In this regard, the turbidity and colorimetric measurements can be taken with a probe tip that has been configured specific to that application. Thus, the present invention contemplates the interchangeability of probe tips that can separately measure fluorescence, turbidity and colorimetry.

For example, the turbidity probe tip can be configured in a similar way as the fluorometric probe tip as discussed above. The difference between the two results in the type of light sources. For the turbidity probe tip, the light source must not cause fluorescence. For highest sensitivity, the aperture is removed. Any suitable light source can be used, such as a UV LED, blue LED or the like. With the turbidity probe tip, a blue light source is preferable. However, the fluorometric probe tip can be interchanged with the turbidity probe tip and vice versa given the self-identifying features as discussed above.

With respect to a colorimetric probe tip, this design is similar to the fluorometric and/or turbidity tip design except that only one filter is necessary. The light source is chosen to correspond to an absorption band of the material in the sample to be detected. In general, a colorimetric amount associated with the sample can be measured by passing an excitation light source, such as a UV LED, though a first filter and then into a detector constructed for that particular type of detection.

It should be appreciated that the mirrors, filters, detectors, excitation light sources, and other suitable components can include a variety of different and suitable commercially available or known products. For example, the detectors are commercially available from Hamamatsu Corporation, 360 Foothill Road, Bridgewater, N.J. 08807 (Part No. S2386-44K); the UV LED source is commercially available from Nichia America Corporation, 3000 Town Center Drive, Southfield, Mich. 48075 (Part No. NSHU590A); and the IR LED source is commercially available from Optek Technology, Inc., 1215 W. Crosby Road, Carrollton, Tex. 75006 (Part No. OP265B).

The present invention can include a variety of different and additional components for optimizing process control, monitoring and/or automation. In an embodiment, the fluorometer includes a printed circuit board assembly connected to a controller, each of a suitable and known construction (not shown). For example, the controller is available from Tecnova, 1486 St. Paul Ave., Gurnee, Ill. 60031 (847)662-6260.

The printed circuit board (PCB) assemblies useful in this device must be fabricated to allow powering by the controller or other device of the components of the fluorometer, which include, for example, drivers for the excitation sources and amplifiers to perform current-to-voltage conversion and signal amplification from the photodetectors. Circuitry to manipulate the signals and communicate the magnitude of the signals is also integral to the PCB. Additional circuitry to measure the temperature and/or the status of the flowswitch may be included.

The fluorometer can be further connected to the controller by a communication cable that enables the controller to electronically communicate with the fluorometer to control the components of the fluorometer as previously discussed. A suitable communication protocol must be selected in order to operate the fluorometer. Suitable standard communication protocols include, but are not limited to, RS-232, I²C, CAN, TCP/IP and a standard RS-485 serial communication protocol. The preferred communication protocol is a standard RS-485 serial communication protocol. It is also possible to use a wireless communication protocol between the fluorometer and controller. One such suitable wireless communication protocol is Bluetooth.

The controller can include isolated, multiple analog inputs. These inputs provide information based on their signal magnitude via 4–20 mA connections. The signals are read by the analog inputs for controlling logic of the controller to provide additional levels of control to, for example, an industrial water system. In a preferred embodiment, the controller has twenty (20) discrete analog inputs.

As previously discussed, the fluorometer of the present invention can be used to monitor and/or detect the presence of one or more fluorophores in a sample derived from any suitable process or system including natural water systems, industrial water systems, or other like sources. Industrial water systems include, but are not limited to, cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

The fluorometer of the present invention can be used in a variety of different industrial water system applications as disclosed, for example, in the following U.S. patent applications.

The instant claimed fluorometer and controller are capable of functioning to control a cooling water system, as described and claimed in U.S. Pat. No. 6,315,909 B1, entitled USE OF CONTROL MATRIX FOR COOLING WATER SYSTEMS CONTROL, issued Nov. 13, 2001, which is herein incorporated by reference in its entirety.

The instant claimed fluorometer and controller are capable of functioning to control a boiler, as described and claimed in U.S. Pat. No. 6,336,058 B1, entitled USE OF CONTROL MATRIX FOR BOILER CONTROL, issued U.S. Pat. No. 6,336,058 B1, issued Jan. 1, 2002, which is herein incorporated by reference in its entirety.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An interchangeable tip-open cell fluorometer comprising:
   a housing and a fluorometric probe tip interchangeably connected to the housing, the probe tip including a probe tip housing defining an open cell and enclosing a probe optical arrangement, the probe optical arrangement including an excitation source and a fluorescence detector wherein the excitation source is aimed at the fluorescence detector such that a sample in the open cell can be fluorometrically detected.

2. The interchangeable tip-open cell fluorometer of claim 1 further comprising an excitation filter and an emission filter each in contact with the sample.

3. The interchangeable tip-open cell fluorometer of claim 2 wherein the excitation filter includes an excitation band and the emission filter includes an emission band, and wherein the excitation band and the emission band are sufficiently separated such that at least a substantial amount of a light beam derived from the excitation source cannot pass through the emission filter to the fluorescence detector.

4. The interchangeable tip-open cell fluorometer of claim 2 wherein the probe optical arrangement includes a second light source in addition to the excitation source that each emits a light beam to the sample via a reflective member at an angle perpendicular to the excitation filter.

5. The interchangeable tip-open cell fluorometer of claim 4 wherein the reflective member includes a dichroic mirror.

6. The interchangeable tip-open cell fluorometer of claim 4 wherein the second light source emits a light beam that can pass through the excitation filter and the emission filter allowing correction to the fluorometric detection due to at least one of fouling and turbidity.

7. The interchangeable tip-open cell fluorometer of claim 2 wherein the excitation source includes a single excitation source that passes an excitation light beam through the excitation filter thereby causing a fluorescent emission derived from the sample, wherein the fluorescent emission passes through the emission filter for detection while the excitation light beam is effectively blocked from passing therethrough, and wherein the single excitation source is aimed directly at the fluorescence detector.

8. The interchangeable tip-open cell fluorometer of claim 2 wherein the probe optical arrangement includes a second light source in addition to the excitation source, wherein the excitation source emits an excitation light beam at an angle perpendicular to the excitation filter, and wherein the second light source emits a second light beam at an angle offset from perpendicular with respect to the excitation filter.

9. The interchangeable tip-open cell fluorometer of claim 8 wherein the second light beam is offset at about 12° or less from perpendicular with respect to the excitation filter.

10. The interchangeable tip-open cell fluorometer of claim 8 wherein the second light beam can pass through the excitation filter and the emission filter such that fluorometric detection can be corrected for at least one of turbidity and fouling.

11. The interchangeable tip-open cell fluorometer of claim 2 wherein the probe optical arrangement includes a second light source in addition to the excitation source such that each passes through the excitation filter at an angle offset from perpendicular with respect to the excitation filter.

12. The interchangeable tip-open cell fluorometer of claim 11 wherein the angle is approximately 9° or less.

13. The interchangeable tip-open cell fluorometer of claim 1 further comprising one or more additional probe tips in addition to the fluorometric probe tip wherein the fluorometric probe tip can be used interchangeably with the one or more additional probe tips.

14. The interchangeable tip-open cell fluorometer of claim 13 wherein the fluorometric probe tip and the one or more additional probe tips are self-identifying allowing the fluorometer to be ready-for-use once a probe tip has been interchanged.

15. The interchangeable tip-open cell fluorometer of claim 13 wherein the one or more additional probe tips at least include a turbidity probe tip and a colorimetric probe tip.

16. A method of fluorometrically detecting fluorophores present in a sample, the method comprising the steps of:
 a) providing a fluorometer, the fluorometer comprising a housing and a fluorometric probe tip interchangeably connected to the housing, the probe tip including a probe tip housing defining an open cell and enclosing a probe optical arrangement, the probe optical arrangement including an excitation source and a fluorescence detector wherein the excitation source is aimed at the fluorescence detector such that a sample in the open cell can be fluorometrically detected;
 b) providing one or more samples derived from a natural or industrial process stream;
 c) using the fluorometer to detect the fluorescent signals of the fluorophores in the samples; and
 d) operating a controller in such a way that the fluorescent signals detected by the fluorometer are used by the controller to monitor and/or control the natural or industrial process from which the samples are taken.

17. The method of claim 16 further comprising an excitation filter and an emission filter each in contact with the sample.

18. The method of claim 17 wherein the excitation filter includes an excitation band and the emission filter includes an emission band, and wherein the excitation band and the emission band are sufficiently separated such that at least a substantial amount of a light beam derived from the excitation source cannot pass through the emission filter to the fluorescence detector.

19. The method of claim 17 wherein the probe optical arrangement includes a second light source in addition to the excitation source that each emits a light beam to the sample via a reflective member at an angle perpendicular to the excitation filter and along substantially the same path.

20. The method of claim 19 wherein the second light source emits a light beam that can pass through the excitation filter and the emission filter allowing correction to the fluorometric detection due to at least one of fouling and turbidity.

21. The method of claim 17 wherein the light source includes a single excitation source that passes an excitation light beam through the excitation filter thereby causing a fluorescent emission derived from the sample, wherein the fluorescent emission passes through the emission filter for detection while the excitation light beam is effectively blocked from passing therethrough, and wherein the single excitation source is aimed directly at the fluorescence detector.

22. The method of claim 17 wherein the probe optical arrangement includes a second light source in addition to the excitation source, wherein the excitation source emits an excitation light beam at an angle perpendicular to the excitation filter, and wherein the second light source emits a second light beam at an angle offset from perpendicular with respect to the excitation filter.

23. The method of claim 22 wherein the second light beam can pass through the excitation filter and the emission filter such that fluorometric detection can be corrected for at least one of turbidity and fouling.

24. The method of claim 17 wherein the probe optical arrangement includes a second light source in addition to the excitation source such that each passes a light beam through the excitation filter at an angle offset from perpendicular with respect to the excitation filter.

25. The method of claim 16 further comprising one or more additional probe tips in addition to the fluorometric probe tip wherein the fluorometric probe tip can be used interchangeably with the one or more additional probe tips.

26. The method of claim 25 wherein the one or more additional probe tips at least include a turbidity probe tip and a colorimetric probe tip.

27. The method of claim 16 wherein the sample is from the water of an industrial process stream wherein the industrial process stream is an industrial water system.

28. The method of claim 27 wherein said industrial process stream is selected from the group consisting of: cooling tower water systems; open recirculating cooling tower water systems; closed cooling two water systems; once-through cooling tower water systems; petroleum wells; downhole formations; geothermal wells; oil field based water system; boilers; boiler water systems; mineral process waters including mineral washing, flotation and benefaction; paper mill digesters; paper mill washers; paper mill bleach plants; paper mill white water systems; black liquor evaporators in the pulp industry; gas scrubbers and air washers; continuous casting processes in the metallurgical industry; air conditioning and refrigeration systems; petroleum process water; indirect contact cooling and heating water, such as pasteurization water; water reclamation and purification systems; membrane filtration water systems; food processing streams; waste treatment systems; clarifiers; liquid-solid applications; municipal sewage treatment; and industrial or municipal water systems.

29. The method of claim 16, wherein step (c) is accomplished by a methodology selected from the group of consisting of: grab-sampling; in-line detection; and in-process detection.

30. The method of claim 16, wherein said excitation source is selected from the group consisting of: a LED source; and a laser source.

31. The method of claim 16, wherein said excitation source is capable of emitting light having a wavelength from about 200 nm to 1200 nm.

32. The interchangeable tip-open cell fluorometer of claim 1, wherein said excitation source is selected from the group consisting of: a LED source; and a laser source.

33. The interchangeable tip-open cell fluorometer of claim 1, wherein said excitation source is capable of emitting light having a wavelength from about 200 nm to 1200 nm.

* * * * *